United States Patent
Izutani et al.

(10) Patent No.: US 10,847,262 B2
(45) Date of Patent: Nov. 24, 2020

(54) MEDICAL IMAGE PROCESSING APPARATUS, MEDICAL IMAGE PROCESSING METHOD AND MEDICAL IMAGE PROCESSING SYSTEM

(71) Applicant: Ziosoft, Inc., Tokyo (JP)

(72) Inventors: Akihiko Izutani, Tokyo (JP); Shinichiro Seo, Tokyo (JP)

(73) Assignee: ZIOSOFT, INC., Tokyo (JP)

(*) Notice: Subject to any disclaimer, the term of this patent is extended or adjusted under 35 U.S.C. 154(b) by 117 days.

(21) Appl. No.: 16/375,932

(22) Filed: Apr. 5, 2019

(65) Prior Publication Data
US 2019/0311795 A1 Oct. 10, 2019

(30) Foreign Application Priority Data

Apr. 10, 2018 (JP) .................. 2018-075474

(51) Int. Cl.
*G16H 30/40* (2018.01)
*G06T 7/00* (2017.01)
(Continued)

(52) U.S. Cl.
CPC .......... *G16H 30/40* (2018.01); *G06T 7/0012* (2013.01); *A61B 5/4312* (2013.01); *G06T 2207/10072* (2013.01); *G16H 30/20* (2018.01)

(58) Field of Classification Search
None
See application file for complete search history.

(56) References Cited

U.S. PATENT DOCUMENTS 5,740,268 A * 4/1998 Nishikawa ............. G06K 9/527
382/130
7,127,090 B2 * 10/2006 Kreang-Arekul ........ G06K 9/32
382/128

(Continued)

FOREIGN PATENT DOCUMENTS

JP H06-269424 A 9/1994
JP 5408493 B2 2/2014

OTHER PUBLICATIONS

Agoston, Tony A., et al., "Intensity-modulated Parametric Mapping for Simultaneous Display of Rapid Dynamic and High-Spatial Resolution Breast MR Imaging Data", Imaging & Therapeutic Technology, vol. 21, No. 1, Jan.-Feb. 2001, pp. 217-226.

*Primary Examiner* — Anand P Bhatnagar
(74) *Attorney, Agent, or Firm* — Pearne & Gordon LLP

(57) ABSTRACT

A medical image processing apparatus includes an acquisition unit and a processing unit. The acquisition unit acquires first and second medical images in time series. The processing unit calculates a first parameter indicating a transition of luminance at a first point based on the luminance at the first point on the first medical image and luminance at a second point on the second medical image, calculates a second parameter indicating a transition of luminance at a third point based on the luminance at the third point on the first medical image and luminance at a fourth point on the second medical image, visualizes the first medical image by superimposing the first parameter on the first point and superimposing the second parameter on the third point; and visualizes the second medical image by superimposing the first parameter on the second point and superimposing the second parameter on the fourth point.

8 Claims, 13 Drawing Sheets

(51) Int. Cl.
*A61B 5/00* (2006.01)
*G16H 30/20* (2018.01)

(56) References Cited

U.S. PATENT DOCUMENTS

| | | | | |
|---|---|---|---|---|
| 8,311,300 B1* | 11/2012 | Matsumoto | G06T 3/0093 | 382/128 |
| 9,138,165 B2* | 9/2015 | Holsing | G06T 19/00 | |
| 9,443,161 B2* | 9/2016 | Guo | G06T 7/73 | |
| 10,140,704 B2* | 11/2018 | Holsing | A61B 8/0841 | |
| 2002/0045153 A1* | 4/2002 | Kaufman | G06K 9/38 | 434/262 |
| 2002/0177149 A1* | 11/2002 | Rimm | G06T 7/0012 | 435/6.16 |
| 2005/0068317 A1* | 3/2005 | Amakai | G06T 7/001 | 345/419 |
| 2005/0255036 A1* | 11/2005 | Flynn | F28G 1/12 | 423/608 |
| 2012/0121155 A1* | 5/2012 | Ruth | G06T 7/0012 | 382/131 |
| 2013/0231556 A1* | 9/2013 | Holsing | A61B 8/0841 | 600/424 |
| 2018/0130204 A1* | 5/2018 | Degani | A61B 5/004 | |
| 2019/0108633 A1* | 4/2019 | Haider | A61B 5/055 | |

* cited by examiner

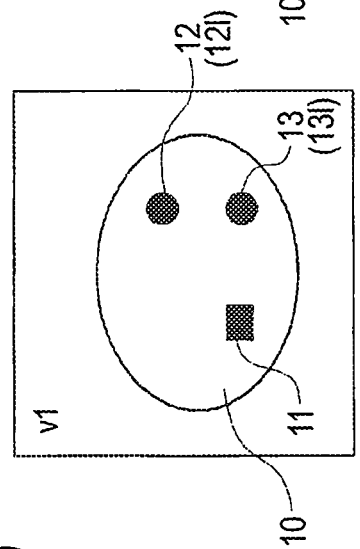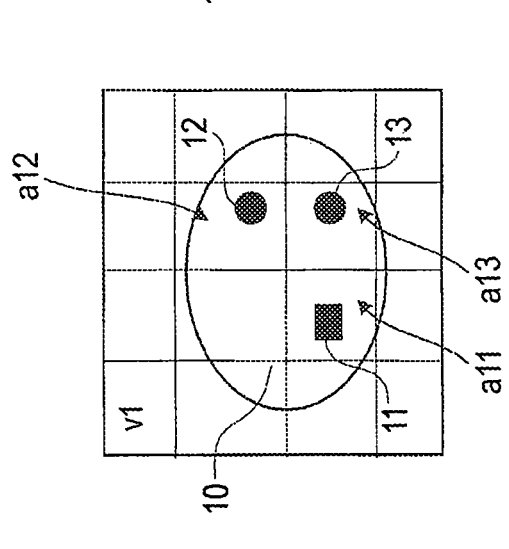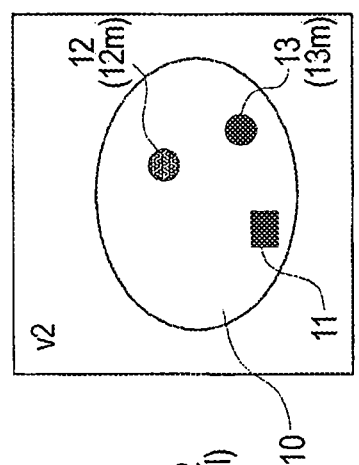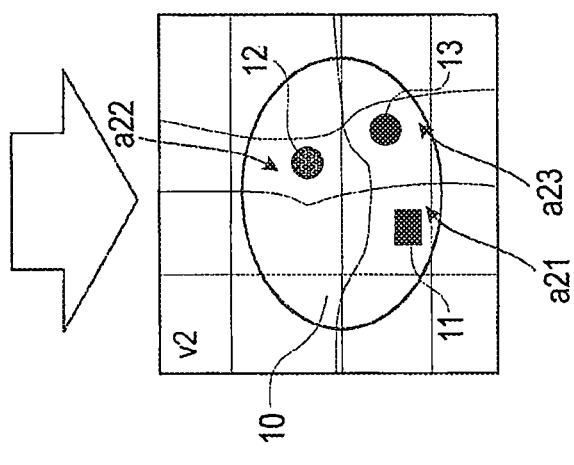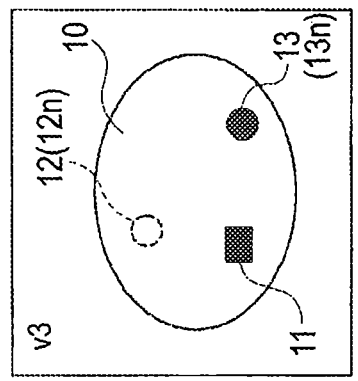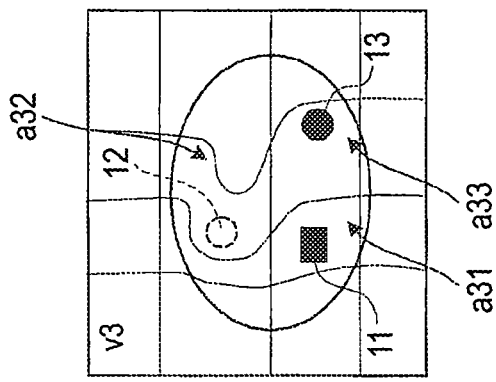
FIG. 10

MEDICAL IMAGE PROCESSING APPARATUS, MEDICAL IMAGE PROCESSING METHOD AND MEDICAL IMAGE PROCESSING SYSTEM

CROSS-REFERENCE TO RELATED APPLICATION

This application claims priority based on Japanese Patent Application No. 2018-075474, filed on Apr. 10, 2018, the entire contents of which are incorporated by reference herein.

BACKGROUND OF THE INVENTION

1. Field of the Invention

The present disclosure relates to a medical image processing apparatus, a medical image processing method, and a medical image processing system.

2. Related Art

In recent years, there are medical image processing apparatuses performing dynamic scanning by injecting a contrast medium into a subject, calculating perfusion based on time-series data obtained by the scanning, and displaying results as numerical values and images (see JP-A-6-269424 and "Intensity-modulated Parametric Mapping for Simultaneous Display of Rapid Dynamic and High-Spatial-Resolution Breast MR Imaging Data").

SUMMARY

In JP-A-6-269424 and "Intensity-modulated Parametric Mapping for Simultaneous Display of Rapid Dynamic and High-Spatial-Resolution Breast MR Imaging Data", perfusion is obtained based on the time-series data by the scanning. Accordingly, when the subject moves during the scanning, the position of the subject in the time-series data changes, which causes perfusion including the movement of the subject and may result in a difference from the true perfusion.

In order to avoid a change in the position of the subject in the time-series data, it is considered to perform registration processing for performing registration on the time-series data in advance. In this case, it is possible to observe a blood stream as perfusion, but the actual movement of the entire subject is suppressed to be in a substantially stationary state. Therefore, it is not possible to observe both the actual movement of the entire subject and blood stream at the same time. In addition, registration processing is a technique in progress and thus may fail. In this case, perfusion may be erroneously visualized, but this could not be always recognizable.

The present disclosure is contrived in view of such circumstances and provides a medical image processing apparatus, a medical image processing method, and a medical image processing system, capable of observing both the movement of a subject and the movement of a fluid inside the subject.

According to one aspect of the disclosure, a medical image processing apparatus includes an acquisition unit and a processing unit. The acquisition unit acquires images of a same subject at least twice in time series to acquire a first medical image and a second medical image. Based on the acquired first and second medical images, the processing unit is configured to calculate a first parameter indicating a transition of luminance at a first point based on the luminance at the first point on the first medical image and luminance at a second point on the second medical image. The first and second points indicate a same tissue. Spatial coordinates of the second point are different from spatial coordinates of the first point. The processing unit is configured to calculate a second parameter indicating a transition of luminance at a third point based on the luminance at the third point on the first medical image and luminance at a fourth point on the second medical image. The third and fourth points indicate a same tissue. Spatial coordinates of the third point are different from spatial coordinates of the fourth points. The processing unit is configured to visualize the first medical image by superimposing the first parameter on the first point and by superimposing the second parameter on the third point in the first medical image. The processing unit is configured to visualize the second medical image by superimposing the first parameter on the second point and by superimposing the second parameter on the fourth point in the second medical image.

BRIEF DESCRIPTION OF THE INVENTION

FIG. 10 is a diagram supplementarily illustrating the generation of a parametric map based on time-series data in terms of registration according to the first embodiment;

DETAILED DESCRIPTION OF THE EMBODIMENT

Hereinafter, an embodiment of the present disclosure will be described with reference to the accompanying drawings.

First Embodiment

In the present disclosure, a medical image processing apparatus includes an acquisition unit, a processing unit and a display. The acquisition unit acquires images of a same subject at least twice in time series to acquire a first medical image and a second medical image. Based on the acquired first and second medical images, the processing unit is configured to calculate a first parameter indicating a transition of luminance at a first point based on the luminance at the first point on the first medical image and luminance at a second point on the second medical image. The first and second points indicate a same tissue. Spatial coordinates of the second point are different from spatial coordinates of the first point. The processing unit is configured to calculate a second parameter indicating a transition of luminance at a third point based on the luminance at the third point on the first medical image and luminance at a fourth point on the second medical image. The third and fourth points indicate a same tissue. Spatial coordinates of the third point are different from spatial coordinates of the fourth points. The processing unit is configured to visualize the first medical image by superimposing the first parameter on the first point and by superimposing the second parameter on the third point in the first medical image, and the display shows the visualized first medical image. The processing unit is configured to visualize the second medical image by superimposing the first parameter on the second point and by superimposing the second parameter on the fourth point in the second medical image, and the display shows the visualized second medical image. According to the disclosure, the medical image processing apparatus can support the observation of both the movement of the subject and the movement of a fluid inside the subject.

Figure 1:
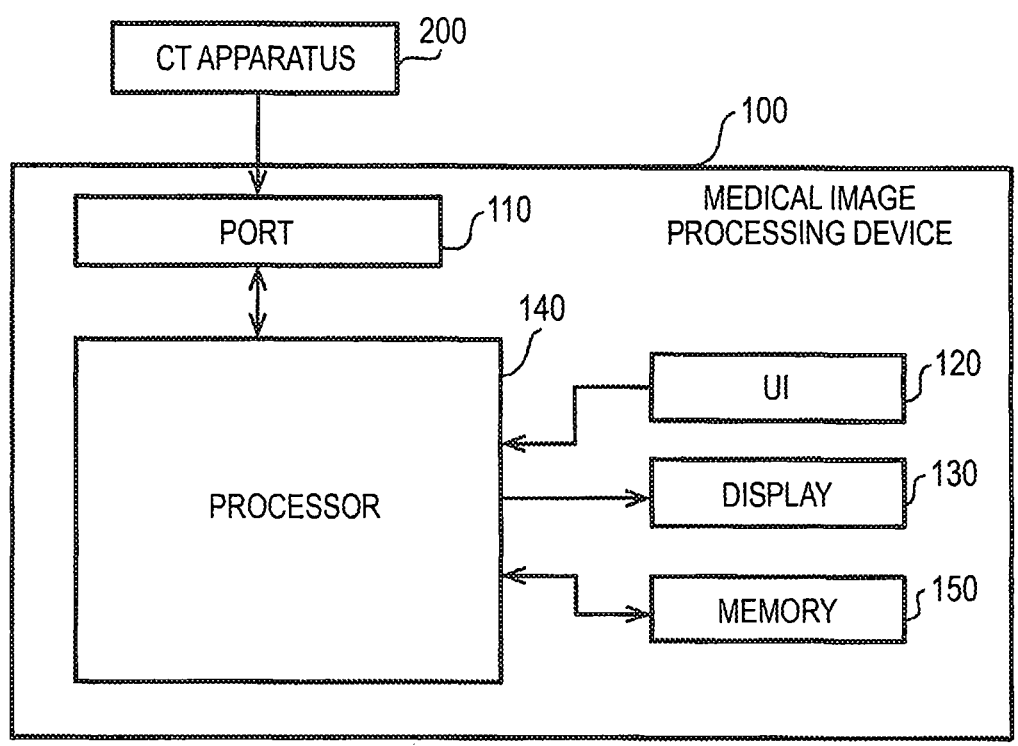
FIG. 1 is a block diagram showing a hardware configuration example of a medical image processing apparatus according to a first embodiment.

FIG. 1 is a block diagram illustrating a configuration example of a medical image processing apparatus 100 according to a first embodiment. The medical image processing apparatus 100 includes a port 110, a user interface (UI) 120, a display 130, a processor 140, and a memory 150.

A CT apparatus 200 is connected to the medical image processing apparatus 100. The medical image processing apparatus 100 acquires volume data from the CT apparatus 200 and processes the acquired volume data. The medical image processing apparatus 100 may be a personal computer (PC) or software installed in the PC.

The CT apparatus 200 irradiates an organism with X-rays to acquire an image (CT image) using a difference in the absorption of X-rays due to tissues in the body. Examples of the organism include a human body and the like. The organism is an example of a subject.

A plurality of CT images may be acquired in time series. The CT apparatus 200 generates volume data including information on any portion inside the organism. The portion inside the organism may include various tissues (for example, a brain, a heart, a kidney, a colon, a small intestine, a lung, a breast, mammary glands, prostate glands, and a lung). By acquiring the CT image, voxel values (CT values) of voxels in the CT image are obtained. The CT apparatus 200 transmits volume data as the CT image to the medical image processing apparatus 100 via wired or wireless.

Specifically, the CT apparatus 200 includes a gantry (not shown) and a console (not shown). The gantry includes an X-ray generator (not shown) and an X-ray detector (not shown), and performs imaging at a predetermined timing instructed by the console to detect X-rays having passed through a human body and to obtain X-ray detection data. The X-ray generator includes an X-ray tube (not shown). The console is connected to the medical image processing apparatus 100. The console acquires a plurality of pieces of X-ray detection data from the gantry and generates volume data based on the X-ray detection data. The console transmits the generated volume data to the medical image processing apparatus 100. The console may include an operation unit (not shown) to input patient information, imaging conditions related to CT imaging, contrast conditions related to administration of a contrast medium, and other information. The operation unit may include an input device such as a keyboard or a mouse.

The CT apparatus 200 can also acquire a plurality of pieces of three-dimensional volume data by continuously performing imaging to generate a moving image. Data regarding a moving image based on the plurality of pieces of three-dimensional volume data is also referred to as four-dimensional (4D) data.

The CT apparatus 200 may acquire CT images at a plurality of timings. The CT apparatus 200 may acquire a CT image in a state where a subject is contrast-enhanced. The CT apparatus 200 may acquire a CT image in a state where a subject is not contrast-enhanced.

The port 110 within the medical image processing apparatus 100 includes a communication port and an external device connection port and acquires volume data from a CT image. The acquired volume data may be immediately transmitted to the processor 140 to be subjected to various processing, or may be stored in the memory 150 and then transmitted to the processor 140 when necessary to be subjected to various processing. In addition, the volume data may be acquired through a recording medium or recording media.

The volume data imaged by the CT apparatus 200 may be transmitted from the CT apparatus 200 to an image data server (picture archiving and communication systems: PACS) (not shown) and stored therein. The port 110 may acquire the volume data from the image data server instead of acquiring the volume data from the CT apparatus 200. In this manner, the port 110 functions as an acquisition unit that acquires various data such as volume data.

The UI 120 may include a touch panel, a pointing device, a keyboard, or a microphone. The UI 120 receives an input from a user of the medical image processing apparatus 100. The user may include a doctor, a radiology technician, or other paramedic staffs.

The UI 120 receives operations such as designation of a region of interest (ROI) and setting of luminance conditions in the volume data. The region of interest may include regions of various tissues (for example, blood vessels, a bronchus, an internal organ, a bone, a brain, a heart, a foot, a neck, and a blood stream). The tissues may broadly include tissues of organism such as lesion tissues, normal tissues, internal organs, and organs. In addition, the UI 120 may receive operations such as designation of a region of interest and setting of luminance conditions in volume data or an image based on the volume data (for example, a three-dimensional image and a two-dimensional image to be described later). While voxel is used for three-dimensional image, pixel is used for two-dimensional image. Transition of luminance can be got from pixel values or voxel values.

The display 130 may include a liquid crystal display (LCD) and displays various pieces of information. The various pieces of information may include a three-dimensional image and a two-dimensional image obtained from volume data. The three-dimensional image may include a volume rendering image, a surface rendering image, a virtual endoscope image (VE image), a curved planar reconstruction (CPR) image, and the like. The volume rendering image may include a ray-sum image (also simply referred to as a "SUM image"), a maximum intensity projection (MW) image, a minimum intensity projection (MinIP) image, an average value (average) image, or a ray-cast image. The two-dimensional image may include an axial image, a sagittal image, a coronal image, a multi-planer reconstruction (MPR) image, and the like. The three-dimensional image and the two-dimensional image may include a color fusion image.

The memory 150 includes various primary storage devices such as a read only memory (ROM) and a random access memory (RAM). The memory 150 may include a secondary storage device such as a hard disk drive (HDD) and a solid state drive (SSD). The memory 150 may include a tertiary storage device such as a USB memory or an SD card. The memory 150 stores various pieces of information and programs. The various pieces of information may include volume data acquired by the port 110, an image generated by the processor 140, setting information set by the processor 140, and various programs. The memory 150 is an example of a non-transitory recording medium in which programs are recorded.

The processor 140 may include a central processing unit (CPU), a digital signal processor (DSP), or a graphics processing unit (GPU). The processor 140 executes a medical image processing program recorded in the memory 150 as a processing unit 160 that performs various processing and control.

Figure 2:
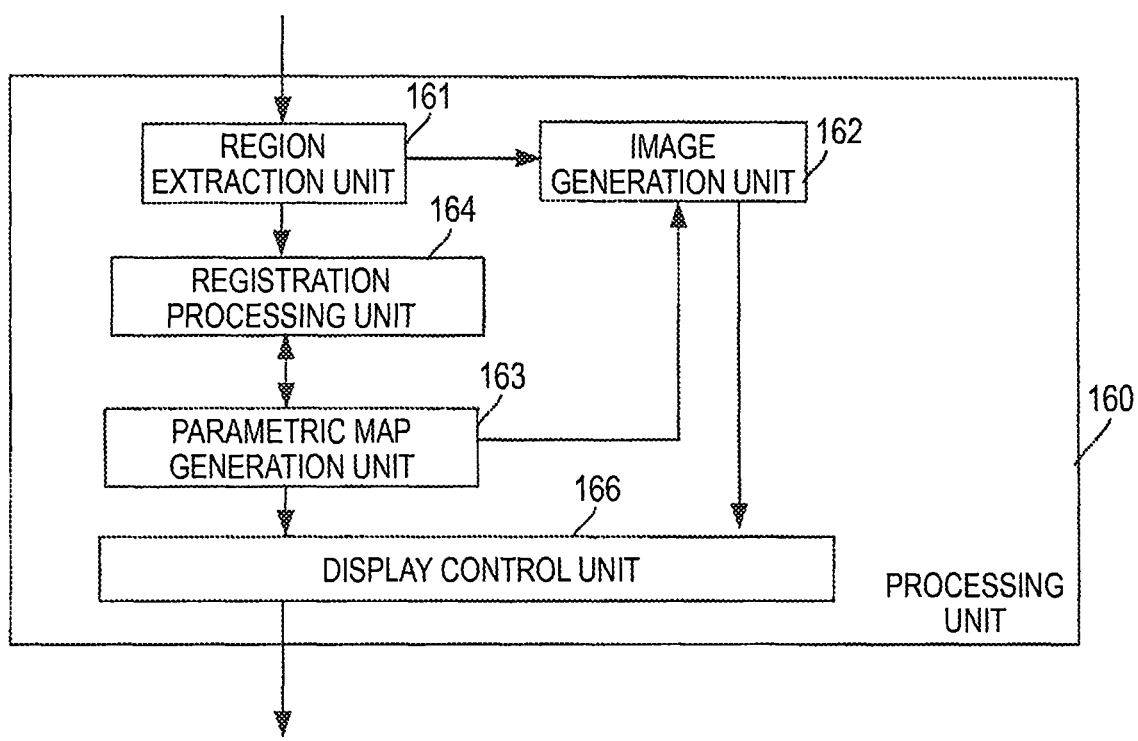
FIG. 2 is a block diagram showing a functional configuration example of the medical image processing apparatus.

FIG. 2 is a block diagram illustrating a functional configuration example of the processing unit 160.

The processing unit 160 includes a region extraction unit 161, an image generation unit 162, a parametric map generation unit 163, a registration processing unit 164, and a display control unit 166.

The processing unit 160 controls each unit of the medical image processing apparatus 100. The units included in the processing unit 160 may be performed as different functions by one piece of hardware or may be performed as different functions by a plurality of pieces of hardware. In addition, the units included in the processing unit 160 may be realized by dedicated hardware parts.

The region extraction unit 161 may perform segmentation processing in volume data. In this case, the UI 120 receives an instruction from a user, and the instructed information is transmitted to the region extraction unit 161. The region extraction unit 161 may perform segmentation processing from the volume data based on the instructed information to extract (segment) a region of interest. In addition, a region of interest may be set manually by a user's detailed instruction. Further, when an object to be observed is determined in advance, the region extraction unit 161 may perform segmentation processing from the volume data without a user's instruction to extract a region of interest including an object to be observed. The region to be extracted may include regions of various tissues (for example, blood vessels, a bronchus, an internal organ, a bone, a brain, a heart, a foot, a neck, a blood stream, mammary glands, a breast, and a tumor).

The image generation unit 162 may generate a three-dimensional image or a two-dimensional image based on volume data acquired by the port 110. The image generation unit 162 may generate a three-dimensional image or a two-dimensional image from the volume data acquired by the port 110 based on a designated region or a region extracted by the region extraction unit 161.

The registration processing unit 164 detects movement of each portion included in volume data based on a plurality of pieces of volume data (CT images) obtained in time series and generates movement information. In this case, the registration processing unit 164 performs movement analysis on deformation of CT images between a plurality of phases based on the CT images of the plurality of phases to acquire movement information in the CT images. A specific technique of the movement analysis is disclosed in, for example, U.S. Pat. No. 8,311,300 and JP-B-5408493. There references are examples of non-rigid body registration but may be used in rigid body registration.

The registration processing unit 164 may acquire information regarding the moving amount of any point of a CT image and information regarding the speed as movement information. When the CT image is partitioned into two-dimensional lattice nodes (k, l) and two-dimensional coordinates in lattice nodes (k, l, t) of a phase t of a two-dimensional lattice are set to be (x, y) by applying the technique disclosed in reference U.S. Pat. No. 8,311,300, the registration processing unit 164 may calculate information on the moving amount related to lattice points of the nodes (k, l) based on a difference between the plurality of nodes (k, l, t) obtained by changing the value of the phase t. In addition, the registration processing unit 164 may calculate speed information by time-differentiating the information on the moving amount. The information on the moving amount and the speed may be indicated by vectors.

When the registration processing unit 164 interpolates the movement information of the two-dimensional lattice with respect to each point of the entire CT image, movement information on each point of the CT image is obtained. When movement information on a predetermined point is applied to each point in a region including an observation part, movement information on each point in the region including the observation part is obtained.

In addition, the registration processing unit 164 may generate movement information based on volume data tk−1, time information thereof tk−1, volume data tk and, and time information thereof tk among pieces of volume data arranged in time series when applying the technique disclosed in reference JP-B-5408493. The movement information may indicate information on a correspondence relationship between corresponding positions on a plurality of pieces of volume data or corresponding objects and information on a process in which a position and an object moves and changes. Voxels of each volume data are indices indicating a position at any time between a time k−1 and a time k.

The registration processing unit 164 is not limited to the technique disclosed in reference U.S. Pat. No. 8,311,300 but may perform movement analysis using other known registration techniques. The medical image processing apparatus 100 can grasp to which position any position inside a subject has moved through movement analysis of each point or an observation part using movement information.

The parametric map generation unit 163 generates a parameter based on time-series volume data or a three-dimensional image or a two-dimensional image based on the time-series volume data, and movement information. In the time-series volume data, the same points of the object are associated with each other based on the movement information, so that a transition of the luminance of the same point of the object is obtained, thereby generating the parameter. The same points of the object are, for example, corresponding points indicating points of the same tissue, and spatial coordinates thereof in a subject may be different. The parameter is calculated for each voxel of volume data or each voxel of a three-dimensional image or for each pixel of a two-dimensional image. The parametric map generation unit 163 may accumulate parameters of respective voxels in response to volume data, the entirety of a three-dimensional image or a two-dimensional image, and an observation part to generate a parametric map of the volume data, the three-dimensional image, or the two-dimensional image.

The registration processing unit 164 deforms the generated parametric map based on movement information. That is, a position corresponding to the volume data, the three-dimensional image, or the two-dimensional image of which the parameter is obtained may move during an imaging time of the CT apparatus 200 due to a body movement of the subject. The registration processing unit 164 may deform the parametric map in accordance with the movement or may change the position in volume data, the three-dimensional image, or the two-dimensional image corresponding to the parameter. In this case, the parametric map generation unit 163 may deform the position indicated by the parameter or the shape of the parametric map, according to the movement of volume data based on, for example, movement information indicating the movement of the volume data.

The image generation unit 162 may superimpose the parametric map generated based on the volume data on at least one piece of volume data among pieces of time-series volume data to generate superimposed volume data. The image generation unit 162 may superimpose the parametric map generated based on the three-dimensional image on at least one three-dimensional image among time-series three-dimensional images to generate a superimposed image. The image generation unit 162 may superimpose the parametric map generated based on the two-dimensional image on at least one two-dimensional image among time-series two-dimensional images to generate a superimposed image.

The display control unit 166 displays various data, information, and images on the display 130. The display control unit 166 may visualize a superimposed image by displaying a superimposed image in which a parameter is superimposed on a three-dimensional image or a two-dimensional image shown on a two-dimensional plane. The display control unit 166 may visualize superimposed volume data in which a parameter is superimposed on volume data shown in a three-dimensional space. In this case, the image generation unit 162 may generate a three-dimensional image or a two-dimensional image on which a parameter is superimposed, based on the superimposed volume data. The display control unit 166 may visualize the superimposed volume data by displaying the generated three-dimensional image or two-dimensional image on which a parameter is superimposed.

The volume data, the three-dimensional image, and the two-dimensional image are examples of a medical image. That is, a parameter or a parametric map is superimposed on a medical image and visualized. Hereinafter, an example in which a parameter or a parametric map is superimposed on volume data or a three-dimensional image will be mainly described, but the present disclosure can also be applied to other medical images.

Note that, although an example in which a CT image as volume data is acquired by the CT apparatus 200 is mainly described, a magnetic resonance imaging (MRI) image as volume data may be acquired by an MRI device 200A (not shown).

Next, details of a parametric map will be described.

A parametric map is an image obtained by acquiring volume data as a plurality of time-series images (images of time series) from, for example, the CT apparatus 200 or the MRI apparatus 200A, calculating a value from a transition of the luminance of each point on the images, and mapping the value. The parametric map may be a map shown in a three-dimensional space or may be a map shown on a two-dimensional plane. The parametric map may include a perfusion image. The perfusion image often indicates a parametric map of which a parameter is derived by performing a deconvolution arithmetic operation from the transition of the luminance of each point, among parametric maps.

The parametric map may be used to observe changes in the luminance of each voxel in time series. Therefore, the parametric map may be used to observe, for example, perfusion of blood stream, a transition of the concentration of a contrast medium, and contraction of a lung. Regarding the lung, for example, the luminance of a voxel becomes higher during contraction, and the luminance of a voxel becomes lower during expansion.

The parametric map may be used to diagnose a lesion. For example, it is possible to diagnose bleeding, infarction, the presence of a tumor within a brain based on the parametric map related to blood stream within the brain. In this case, brain CT/MR perfusion may be used. In addition, for example, it is possible to diagnose the presence of breast cancer, calcification, and the like by changes in the luminance of each voxel according to blood stream and the movement of a contrast medium in a breast including mammary glands. For example, when an affected part includes cancer, a blood stream become active and, therefore, the luminance tends to increase. Further, when an affected part includes an infarction portion, a fluid hardly flows around the infarction portion and, therefore, the luminance tends to decrease. The medical image processing apparatus 100 can support accurate diagnose by a doctor by providing the doctor with a parametric map by visualization.

A parametric map and perfusion may include, for example, wash-in, washout, time to peak, mean transit time (MTT), a blood stream (for example, a cerebral blood stream in a brain), a blood volume (a cerebral blood volume in a brain), a maximum slope, T1, T2, and T2* (normally, T1 emphasis, T2 emphasis) in MRI, and an apparent diffusion coefficient (ADC).

Next, specific examples of a three-dimensional image and a parametric map thereof will be described. Here, a breast including mammary glands is assumed to be an observation part, and it is assumed that a contrast medium is administered to the breast and a state where the contrast medium flows is observed using a three-dimensional image and a parametric map obtained in a plurality of phases. Here, it is assumed that an observation part including mammary glands is imaged by the MRI apparatus 200A for approximately 5 minutes of imaging time.

Figure 3:
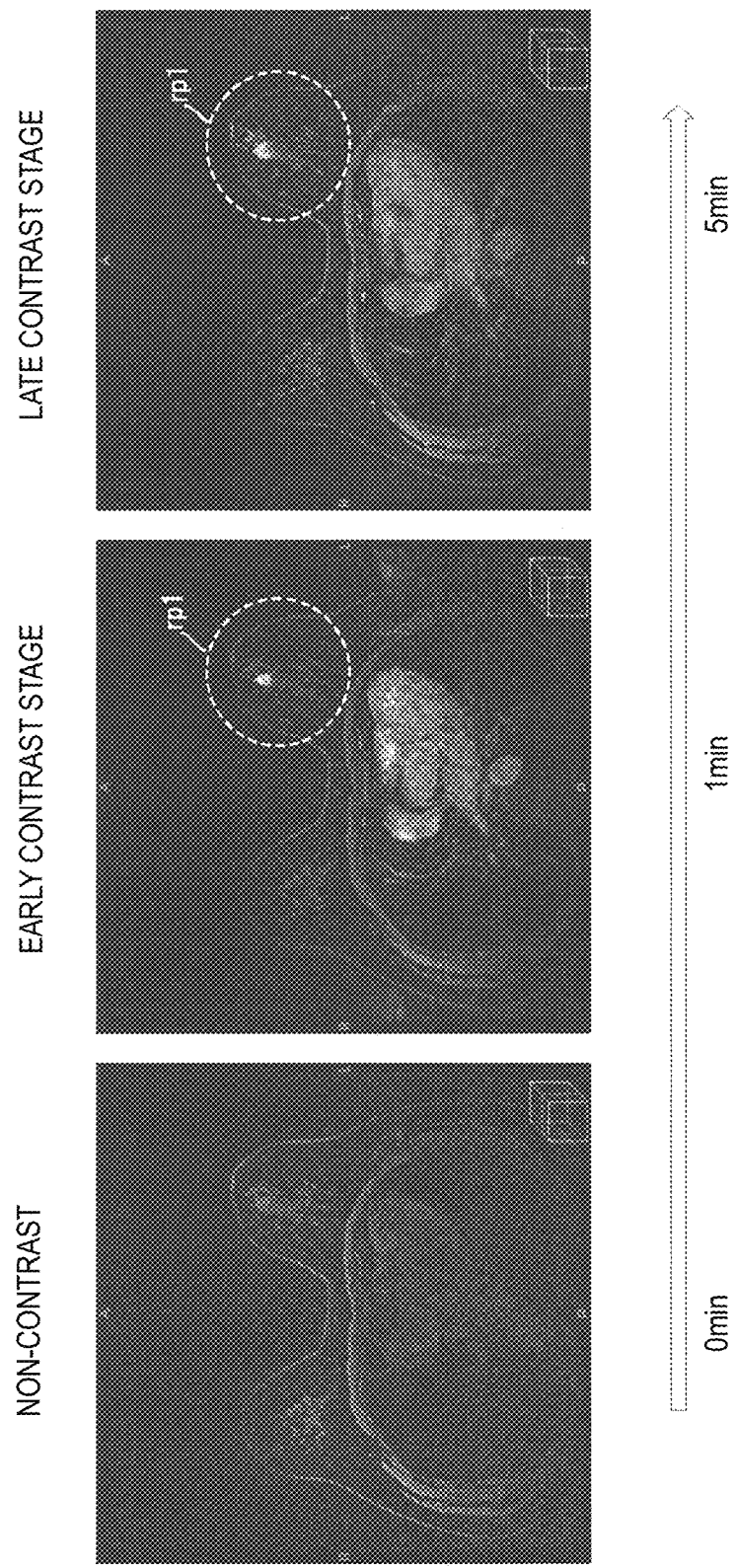
FIG. 3 is a view showing medical images based on volume data in time series, the volume data being data obtained by imaging an observation part including mammary glands in a non-contrast state, an early contrast state, and a late contrast state.

FIG. 3 is a view illustrating an example of a three-dimensional image based on volume data in time series, the volume data being data obtained by imaging an observation part including mammary glands in a non-contrast state, an early contrast state, and a late contrast state. The port 110 acquires volume data of a plurality of phases as time-series data. The image generation unit 162 generates a three-dimensional image based on each volume data.

A horizontal axis in FIG. 3 represents elapsed time (unit: minute (min)) from the start of administration of a contrast medium to a subject. That is, after 0 minutes from the administration of the contrast medium, it becomes a non-contrast state in which the contrast medium does not reach the observation part illustrated in FIG. 3. After 1 minute from the administration of the contrast medium, it becomes an early contrast stage in which the contrast medium reaches the observation part and starts to flow in, and for example, the luminance of a portion of a right breast rp1 is increased. After 5 minutes from the administration of the contrast medium, it becomes a late contrast state in which the contrast medium stops flowing in after reaching the observation part. In the late contrast state, the luminance of a portion of the right breast rp1 is increased, and the luminance of the surrounding mammary glands is also higher than in the early contrast stage.

Figure 4:
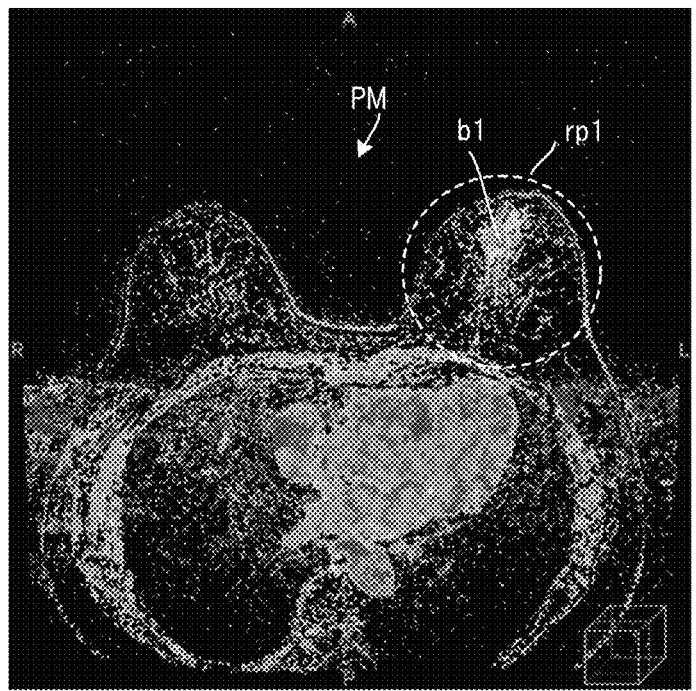
FIG. 4 is a view showing an example of a parametric map in an observation part including breasts.

FIG. 4 is a diagram illustrating an example of a parametric map PM in an observation part including breasts. In the parametric map PM of FIG. 4, for example, transitions (change) of luminance from the early contrast stage to the late contrast stage are shown by purple, blue, light blue, green, yellow, orange, and red in the order of the smallest transition in a stepwise manner (wash out). For example, a part b1 in the right breast rp1 is a portion having colors of green to light blue and has a relatively small transition of luminance. As a result, a doctor can make a remark on a suspected tumor. The parametric map generation unit 163 may perform classification based on a transition of luminance and display portions in different display modes (for example, division of colors) in accordance with classification results.

Figure 5:
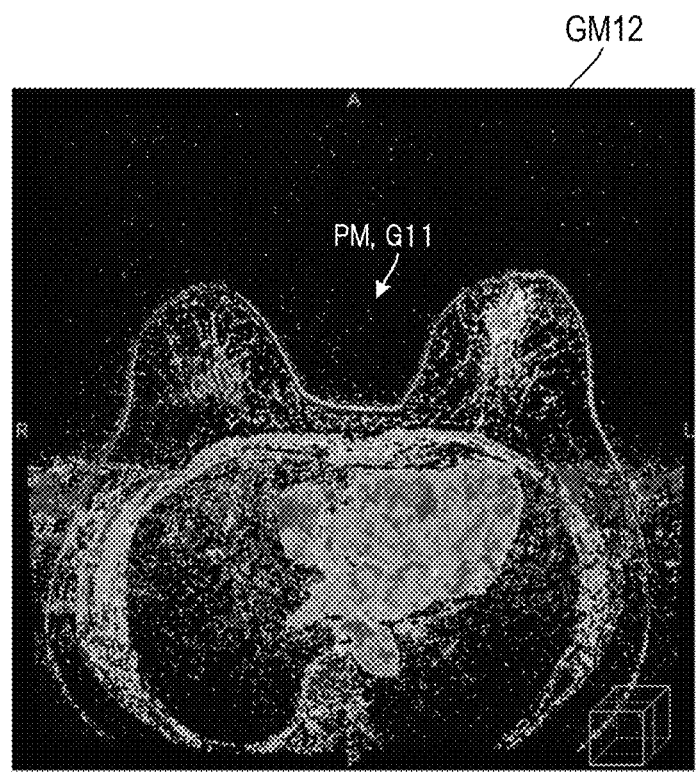
FIG. 5 is a view showing an example of a superimposed image in which a parametric map in the observation part including breasts is superimposed on a non-contrast image of the observation part.

FIG. 5 is a diagram illustrating an example of a superimposed image G12 in which the parametric map PM in the observation part including breasts is superimposed on a non-contrast image G11 of the observation part by alpha-blending. Similarly to the parametric map PM of FIG. 4, the parametric map PM of FIG. 5 has a parameter for each voxel inclusive of voxels having small changes in luminance, and a parameter is shown for each voxel. The proportion of alpha-blending can be arbitrarily operated.

Figure 6:
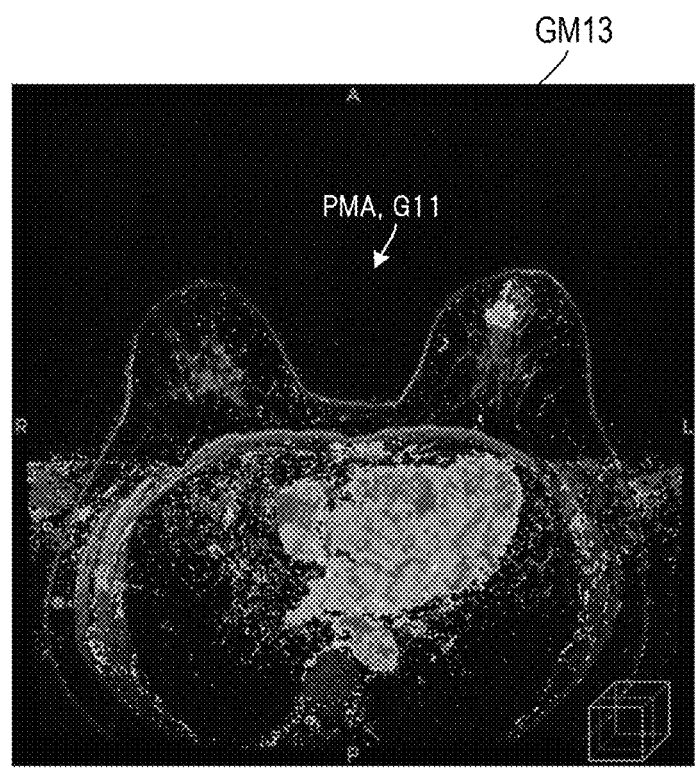
FIG. 6 is a view showing an example of a superimposed image in which a parameter in a parametric map in the observation part including breasts is cut by a threshold value and the parametric map is superimposed on a non-contrast image of the observation part.

FIG. 6 is a diagram illustrating an example of a superimposed image G13 in which a parametric map PMA in the observation part including breasts is superimposed on the non-contrast image G11 of the observation part. The parametric map PMA is a map obtained by cutting the parameter in wash-in by a threshold value th1 with respect to the parametric map PM (washout).

In FIG. 6, for example, the expression of a parameter of a portion not satisfying the threshold value th1 is omitted. Therefore, a washout value (the luminance of a voxel indicating washout) is displayed with respect to only a region having a high wash-in value (the luminance of a voxel indicating wash-in). Thus, the parametric map PMA includes voxels of which the parameters are not expressed, and the non-contrast image G11 corresponding to the parametric map PMA can also be partially visually recognized. Therefore, when visualization is limited to a specific affected part or the state of luminance of a subject is also confirmed through the non-contrast image G11, the visualization method of FIG. 6 is effective.

Next, specific examples of a region of interest (ROI) and a time intensity curve (TIC) will be described.

Figure 7:
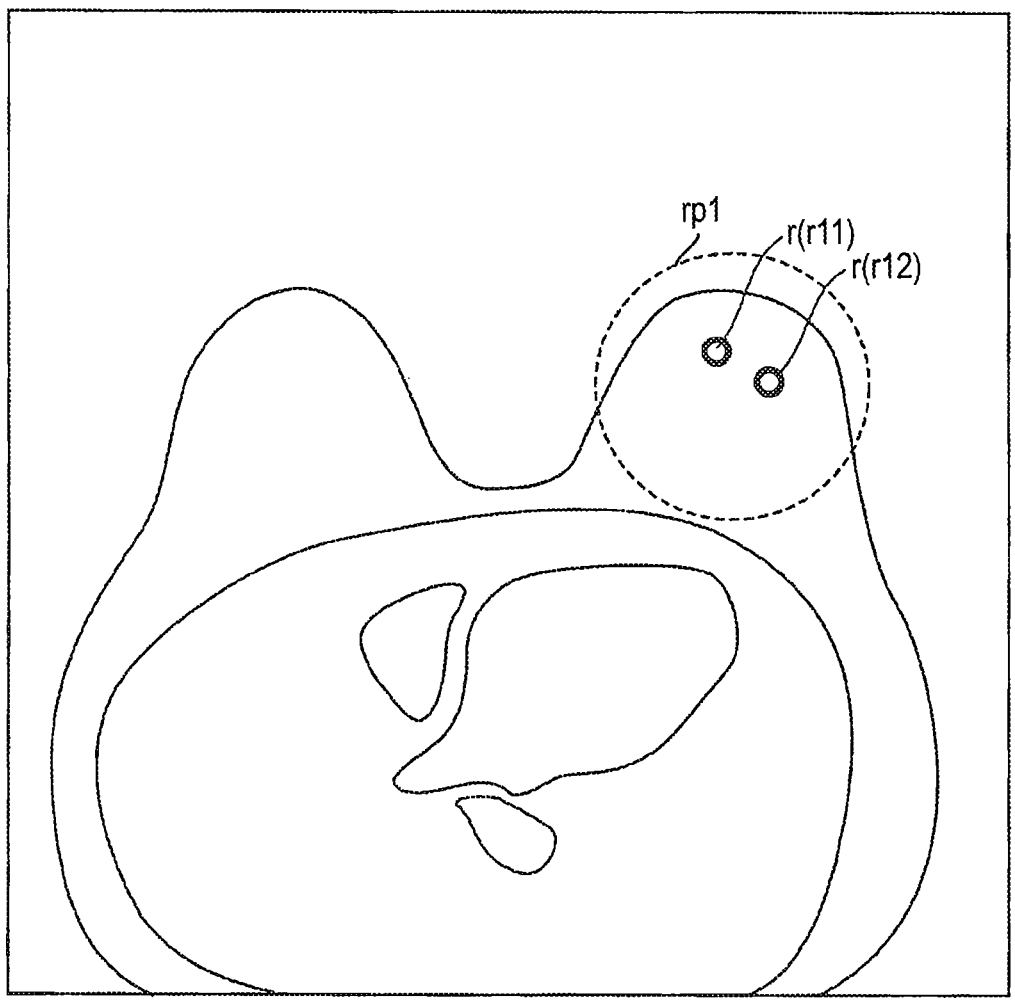
FIG. 7 is a diagram showing an example of regions of interest in breasts.

FIG. 7 is a diagram illustrating an example of regions of interest r in breasts. In FIG. 7, regions of interest r11 and r12 are set as the regions of interest r, for example, through the UI 120. The display 130 may display the set regions of interest r11 and r12 to be superimposed on a three-dimensional image including breasts. The regions of interest r11 and r12 may be expressed to finely express the contours of the regions of interest r11 and r12 through the UI 120 or may be expressed in a primitive shape such as a circular shape or a rectangular shape.

Figure 8:
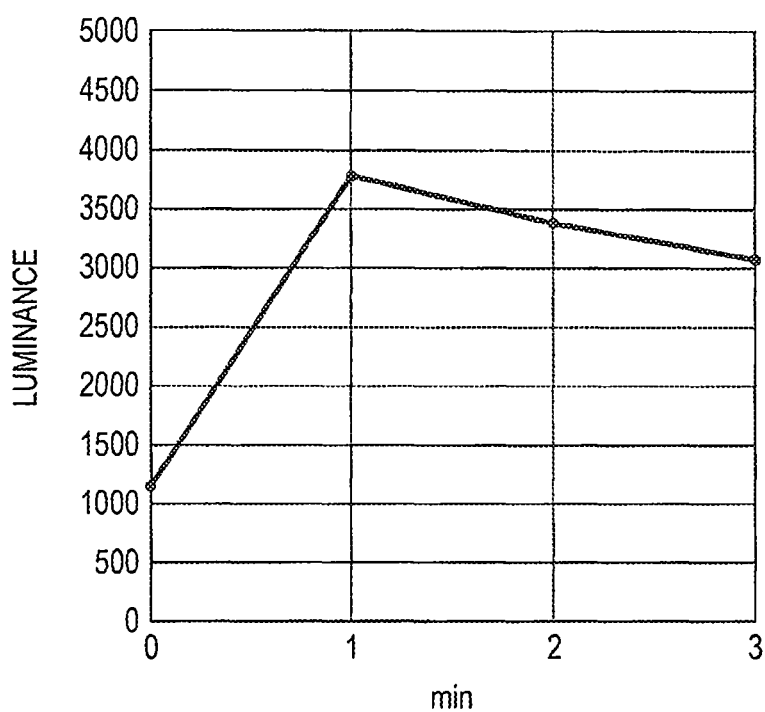
FIG. 8 is a diagram showing an example of a time intensity curve (TIC) at the position of the region of interest.

FIG. 8 is a diagram illustrating an example of a time intensity curve (TIC) at the position of the region of interest r. The TIC is a graph illustrating a transition of the luminance of each point (voxel) on volume data, a three-dimensional image, or a two-dimensional image. In FIG. 8, as an example, a TIC in the region of interest r11 is illustrated. When a TIC in the region of interest r12 is illustrated at the same time, the number of graphs of TICS is two. In addition, the TIC of the region of interest r11 and the TIC of the region of interest r12 may be switched and displayed one by one.

A horizontal axis in FIG. 8 represents elapsed time (unit: minute (min)) from the start of administration of a contrast medium to a subject. A vertical axis in FIG. 8 represents the luminance of the region of interest r. That is, in FIG. 8, the luminance of a tissue existing at the position of the region of interest r in the subject is shown in the non-contrast state after 0 minutes from the administration of the contrast medium, and the luminance is relatively low. The contrast medium flows in at the position of the region of interest r in the early contrast state after 1 minute from the start of administration of the contrast medium, which makes it a high luminance state. The concentration of the contrast medium decreases toward the late contrast state after one minute from the start of administration of the contrast medium, and thus the luminance decreases.

In FIG. 8, changes in the concentration of the contrast medium are shown by a TIC. The parametric map generation unit 163 calculates changes in the concentration of the contrast medium expressed by a TIC as parameters. The parametric map generation unit 163 may calculate a parameter based on the changes in the concentration of the contrast medium using various techniques. For example, the parametric map generation unit 163 may calculate a parameter based on a difference between a maximum value and a minimum value of changes in the concentration of the contrast medium. For example, the parametric map generation unit 163 may calculate a parameter based on the speed of a change in the contrast medium. For example, the parametric map generation unit 163 may calculate a parameter based on other criteria regarding a change in the contrast medium.

Next, details of the region of interest r will be described.

The region of interest r may dynamically move. For example, in a three-dimensional image based on volume data obtained in a plurality of phases, a position indicated by the same region of interest r may be moved by the body movement of a subject. The dynamically moving region of interest r is also referred to as a dynamic ROI (D-ROI). Information on the movement of the region of interest r corresponds to movement information generated by the registration processing unit 164.

The registration processing unit 164 may move the position of the region of interest r in a three-dimensional image based on a plurality of pieces of volume data obtained in time series based on the movement information. Therefore, the medical image processing apparatus 100 can change the position of the region of interest r according to the body movement of the subject. That is, the registration processing unit 164 may adjust and registrate the position of at least one region of interest r of a three-dimensional image of a plurality of phases.

The region extraction unit 161 sets the region of interest r through the UI 120 in one phase among the plurality of phases. A reference phase for setting the region of interest r may be, for example, an image of the early contrast phase for obtaining an image in the early contrast state (for example, an image after one minute from the start of administration of the contrast medium). Since an artery is shown in the early contrast phase, information useful for many diagnoses is included.

The registration processing unit 164 may set the region of interest r based on the movement information in another phase among the plurality of phases. That is, the region of interest r may be set manually in the reference phase and may be set automatically in the other phases based on the movement information.

A user can determine whether or not the generated movement information is accurate by comparing an image of a part existing in the region of interest r in which the position moves between a plurality of phases and the movement of the moving region of interest r. In this case, the user can move the region of interest r in a phase in which the user determines that the movement information is not accurate through the UI 120.

When it is determined that a registration function of the region of interest r is not correctly operated, the registration processing unit 164 may regenerate movement information using the region of interest r which is moved by the user through the UI 120. As a result, more accurate movement information is obtained. In addition, the parametric map generation unit 163 may further calculate a parameter again based on the regenerated movement information to generate a new parametric map.

For example, the parametric map generation unit 163 may calculate a parameter of the region of interest r11 based on the luminance of the region of interest r11 in the reference phase and the luminance of a region of interest r21 (not shown) corresponding to the region of interest r11 in a phase other than the reference phase. The regions of interest r11 and r21 may indicate the same tissue (for example, a tumor to be observed). When a user desires to finely adjust the region of interest r21, the user changes and finely adjusts the position (for example, coordinates) of the region of interest r21 through the UI 120. The parametric map generation unit 163 may calculate a parameter of the region of interest r11 again based on the luminance of the region of interest r11 in the reference phase and the luminance at a position where the region of interest r21 is changed in a phase other than the reference phase. As a result, movement information matching the present state of the subject is obtained.

The parametric map generation unit 163 may collect transitions of the voxels included in the region of interest r and may derive (for example, calculate) a parameter based on collecting results. For example, the parametric map generation unit 163 may generate a TIC based on transitions of the voxels included in the region of interest r. The TIC may be displayed by the display 130. When only a parameter in the region of interest r is necessary, it may be sufficient with the display of the TIC. The TIC is an example of a parameter. The parametric map generation unit 163 may derive a parameter using a statistic value such as an average value or a maximum value of phases of the voxels included in the region of interest r as a voxel value. For example, the parametric map generation unit 163 may generate a TIC based on transitions of voxels by using a statistic value such as an average value or a maximum value of phases included in the region of interest r as a voxel value.

Next, registration processing of the parameter or the parametric map PM of the present embodiment will be described.

The registration processing unit 164 deforms the generated parametric map PM based on the movement information. When a transition of luminance in an internal organ to be observed is observed or when the internal organ is moving in association with body movement of a subject, the parametric map PM can be made to follow the movement of the internal organ.

For example, when a transition of the luminance of a breast including mammary glands in a three-dimensional image is observed, an imaging time of the MRI apparatus 200A is approximately 5 minutes. For this reason, it is considered that a moving subject is present within the imaging time. In this case, the position of the breast may be deformed including movement, within a three-dimensional image of a plurality of phases. Further, when a transition of the luminance of a head in a three-dimensional image is observed and when a subject has a stroke, the subject may move due to convulsion during the imaging time. In this case, the position of the head may be deformed including movement, within a three-dimensional image of a plurality of phases.

For example, when a transition of the luminance of a heart in a three-dimensional image is observed, the heart contracts or expands due to pulsation, and, therefore, the heart is deformed or moved. Further, when a transition of the luminance of a liver in a three-dimensional image is observed, the liver may be moved due to breathing.

For example, the registration processing unit 164 may calculate the movement of a tissue between three-dimensional images or volume data of two phases and may generate movement information based on calculation results. The registration processing unit 164 may deform the parametric map PM according to the deformation of the volume data or the three-dimensional image based on the movement information. The movement information may be generated based on the movement of a tissue between three-dimensional images or volume data of three or more phases.

Next, the details of visualization will be described.

In the visualization of volume data, a portion (2D portion) corresponding to the two-dimensional plane may be extracted from the volume data, and the parametric map PM may be displayed to be superimposed on the two-dimensional plane. That is, the display control unit 166 may display the parametric map PM to be superimposed on a two-dimensional image (for example, an MPR image) which is expressed in a two-dimensional plane.

In addition, when the parametric map PM is superimposed and displayed in the entire region of volume data or a two-dimensional image, it may become difficult to visually recognize the display of luminance of the volume data. The display control unit 166 may superimpose and display a portion of a parameter having a value suspected of a lesion in the parametric map PM and may not superimpose to display a portion of the parameter having a value not suspected of a lesion (that is, a normal value). The value suspected of a lesion varies depending on a tissue or the like. In addition, the display control unit 166 may determine whether to perform superimposed display based on a specific value to be noticed other than a lesion. In addition, the display control unit 166 may determine the range of the superimposed display by using parameters of different parametric maps in the parametric map PM (see FIG. 6).

When the parametric map PM is displayed to be superimposed on the volume data, the display control unit 166 may generate superimposed volume data or a superimposed image based on, for example, an image fusion method. The image fusion method may include, for example, a blending.

In addition, the display control unit 166 may display the parametric map PM to be superimposed on a volume rendering image as a three-dimensional image. In this case, the display control unit 166 may display the parametric map PM to be superimposed on the volume rendering image, for example, by adding a parameter as color information at the time of calculation of surface reflected light.

Next, operations of the medical image processing apparatus 100 will be described.

Figure 9:
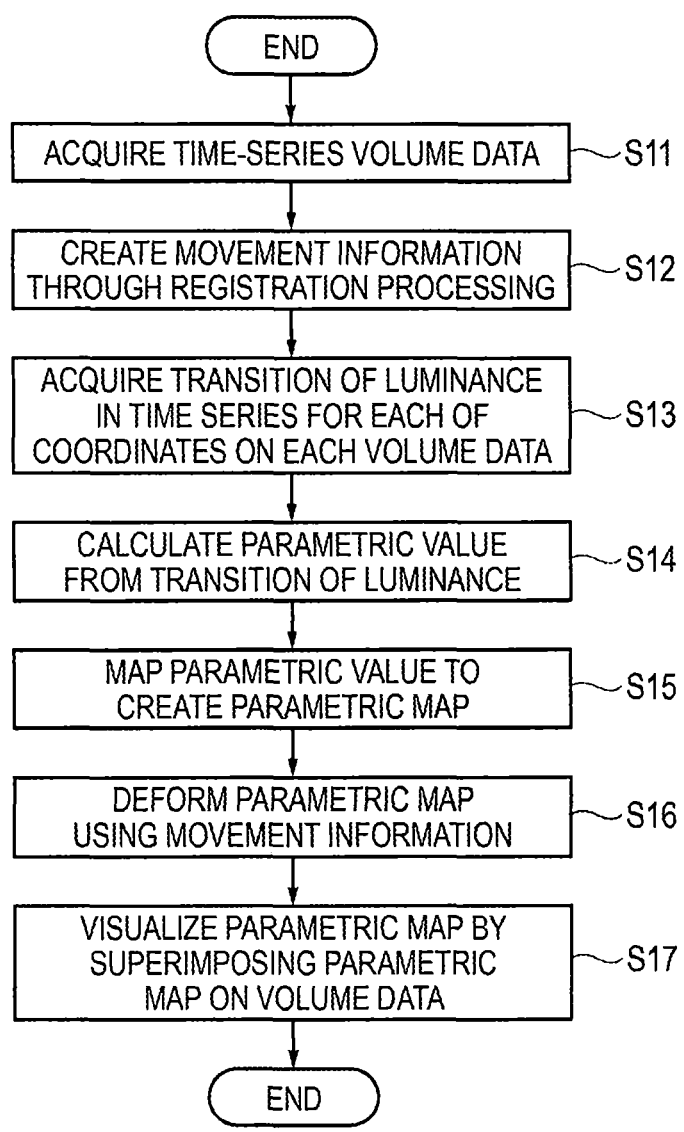
FIG. 9 is a flowchart showing an example of an operation procedure of the medical image processing apparatus according to the first embodiment.

FIG. 9 is a flowchart illustrating an operation example of the medical image processing apparatus 100.

First, the port 110 acquires volume data of a plurality of phases which are arranged in time series from the CT apparatus 200 (S11). The registration processing unit 164 generates movement information based on the acquired volume data of the plurality of phases (S12).

The parametric map generation unit 163 acquires the luminance of each voxel (a luminance component related to a voxel value) in the volume data of the plurality of phases. The parametric map generation unit 163 derives (for example, calculates) a transition of the luminance of the voxel at the corresponding point using the time-series movement information in the volume data of the plurality of phases for each voxel of any phase (S13). Accordingly, the medical image processing apparatus 100 can derive a transition of the luminance of voxels of the same tissue by tracking the same tissue in time series from the movement information.

The parametric map generation unit 163 calculates a parameter based on time-series transitions of the luminance of the voxel at the corresponding point for each voxel (S14). The parametric map generation unit 163 maps a parameter of each voxel to generate a parametric map PM corresponding to the entirety or a portion of the volume data (S15).

For example, the pieces of volume data of the plurality of phases are set to be volume data vd1 and volume data vd2. A luminance value of a voxel (x1, y1, z1) on the volume data vd1 is set to be vd1 (x1, y1, z1). A luminance value of a voxel (x2, y2, z2) on the volume data vd2 is set to be vd2 (x2, y2, z2). The coordinates (x1, y1, z1) and the coordinates (x2, y2, z2) indicate the same point of a moved tissue. In this case, the parametric map generation unit 163 may generate a parametric map PM and a parameter vp (x, y, z) according to the following (Expression 1). The parametric map PM is obtained by mapping the parameter vp at each position.

$$vp(x1,y1,z1)=(vd2(x2,y2,z2)-vd1(x1,y1,z1))/vd1(x1,y1,z1) \quad \text{(Expression 1)}$$

That is, here, the rate of change in the luminance of the reference volume data vd1 is shown as a parameter vp (x 1, y 1, z 1).

The registration processing unit 164 deforms the parametric map PM corresponding to time-series phases based on the movement information (S16). The display control unit 166 visualizes the deformed parametric map PM to be superimposed on the volume data (S17). In this case, the display control unit 166 makes a deformation state of the parametric map PM different for each phase. The display control unit 166 may display the deformed parametric map PM to be superimposed on the volume data for each phase.

The visualization may indicate that superimposed volume data is generated by superimposing each parameter included in the parametric map PM on each voxel of the volume data. In addition, the visualization may indicate that a superimposed image is generated by superimposing each parameter included in the parametric map PM on each voxel of a three-dimensional image or a two-dimensional image based on the volume data. The superimposed image is displayed by the display 130.

Figure 11:
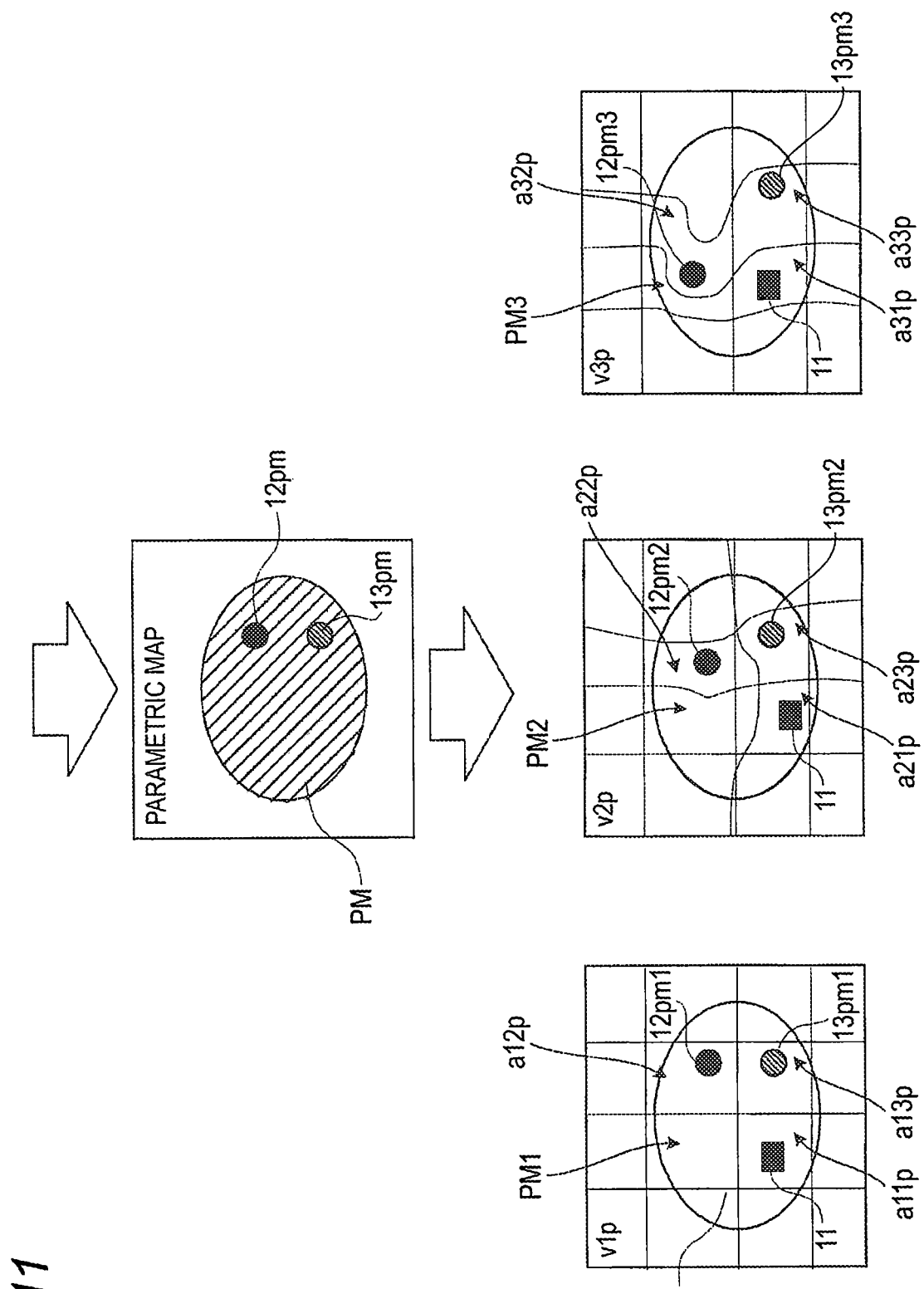
FIG. 11 is a diagram supplementarily illustrating the generation of a parametric map based on time-series data in terms of registration according to the first embodiment (continuation of FIG. 10)

FIGS. 10 and 11 are diagrams supplementarily illustrating the generation of a parametric map PM based on time-series data to which the registration according to the present embodiment is added.

In FIGS. 10 and 11, the port 110 acquires pieces of volume data v1, v2, and v3 as time-series data. The volume data v1 is obtained in a phase f1, the volume data v2 is obtained in a phase f2, and the volume data v3 is obtained in a phase f3. The phases f1 to f3 are continuous in time series. In the pieces of volume data v1 to v3, predetermined cross-sections and faults of a subject 10 as a subject are visualized (displayed). The region of the subject 10 includes an internal organ 11 moving independently of a lesion and affected parts 12 and 13 suspected to have a lesion.

Comparing the pieces of volume data v1 to v3 of the phases with each other, the luminance of voxels does not change much in the internal organ 11, the affected part 13, and the vicinities thereof, and the luminance of voxels changes greatly in the affected part 12 and the vicinity thereof. The change of a circle mark, which indicates the affected part 12, from a black circle to a dashed line indicates a change in the luminance of a voxel.

The registration processing unit 164 generates movement information based on the pieces of volume data v1 to v3. In FIG. 10, when reference volume data is set to be the volume data v1, for example, regions a11, a12, and a13 in the volume data v1 respectively correspond to regions a21, a22, and a23 in the volume data v2 and regions a31, a32, and a33 in the volume data v3. The region a11 is a region including the internal organ 11, the region a12 is a region including the affected part 12, and the region a13 is a region including the affected part 13.

The parametric map generation unit 163 generates a parametric map PM based on the pieces of volume data v1, v2, and v3. The parametric map PM includes a parameter 12pm corresponding to the affected part 12 and a parameter 13pm corresponding to the affected part 13. For example, in FIG. 11, the parameters 12pm and 13pm are different values, indicate, for example, transitions of concentrations of different contrast mediums and have different display modes. The affected part 12 and the affected part 13 have different parameters, and thus may be displayed in display modes corresponding to the parameters, that is, different display modes.

In the parametric map PM, parameters meaningful for diagnosis (for example, the parameters 12pm and 13pm corresponding to the affected parts 12 and 13) may be highlighted, and portions of parameters less meaningful for diagnosis may be highlighted with respect to the luminance of the pieces of volume data v1 to v3. For example, the display control unit 166 highlights parameters when the parametric map PM indicates wash-out and the value of wash-in is equal to or greater than a threshold value th1. In addition, the display control unit 166 further highlights parameters when a parameter of a wash-out parametric map indicates wash-out (instead of Persistent or Plateau).

The parametric map generation unit 163 deforms the parametric map PM based on the movement information. In this case, when a parametric map PM1 corresponding to the reference volume data v1 in FIG. 11 serves as a reference, the parametric map is deformed so that regions a11$p$, a12$p$, and a13$p$ in the parametric map PM1 are respectively regions a21$p$, a22$p$, and a23$p$ in a parametric map PM2 and regions a31$p$, a32$p$, and a33$p$ in a parametric map PM3. This is to cope with the deformation of a region in volume data which is the base of the movement information.

In the parametric maps PM1 to PM3, the calculation of a parameter corresponding to the internal organ 11, and the like are omitted, but the calculation of a parameter corresponding to the internal organ 11, and the like may be performed in the same manner as the affected parts 12 and 13.

The image generation unit 162 generates pieces of superimposed volume data v1$p$, v1$p$, and v3$p$ by superimposing (synthesizing) the parametric maps PM1 to PM3 on the pieces of volume data v1 to v3. In FIG. 11, the internal organ 11, a parameter 12$pm$1 corresponding to the affected part 12, and a parameter 13$pm$1 corresponding to the affected part 13 are visualized in the superimposed volume data v1$p$. In the superimposed volume data v2$p$, the internal organ 11, a parameter 12$pm$2 corresponding to the affected part 12, and a parameter 13$pm$2 corresponding to the affected part 13 are visualized. In the superimposed volume data v3$p$, the internal organ 11, a parameter 12$pm$3 corresponding to the affected part 12, and a parameter 13$pm$3 corresponding to the affected part 13 are visualized. That is, the positions of the parameters 12$pm$2, 12$pm$3, 13$pm$2, and 13$pm$3 are moved following the movement of the affected parts 12 and 13, and thus it is possible to be understood that the parametric maps PM2 and PM3 are deformed.

All of the pieces of superimposed volume data v1$p$ to v3$p$ corresponding to the pieces of volume data v1 to v3 are not required to be generated, and at least one of the pieces of superimposed volume data v1$p$ to v3$p$ may be generated.

Next, the generation of a parametric map PMx in a comparative example will be described.

Figure 12:
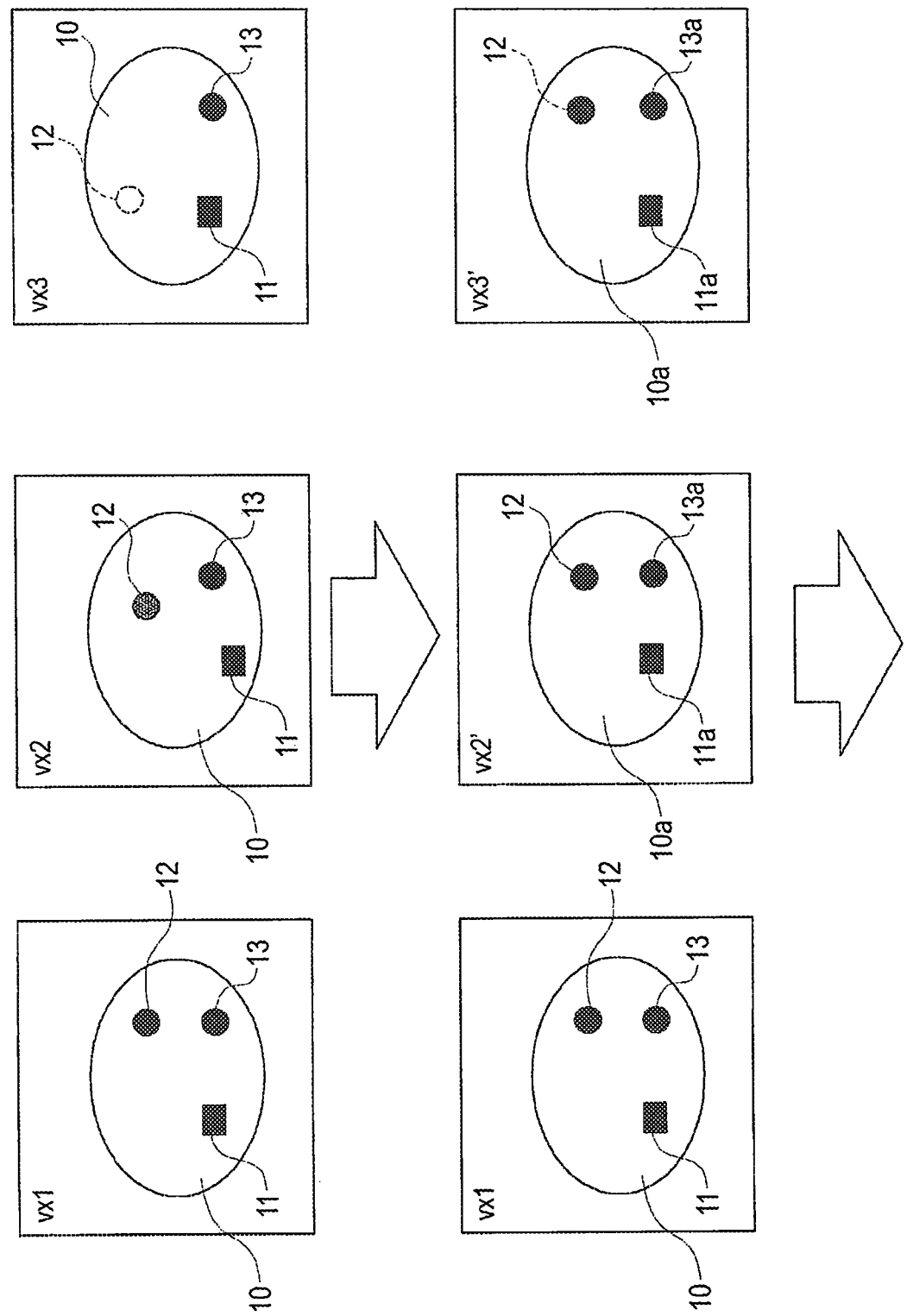
FIG. 12 is a diagram illustrating the generation of a parametric map based on time-series data in terms of registration in a comparative example.
Figure 13:
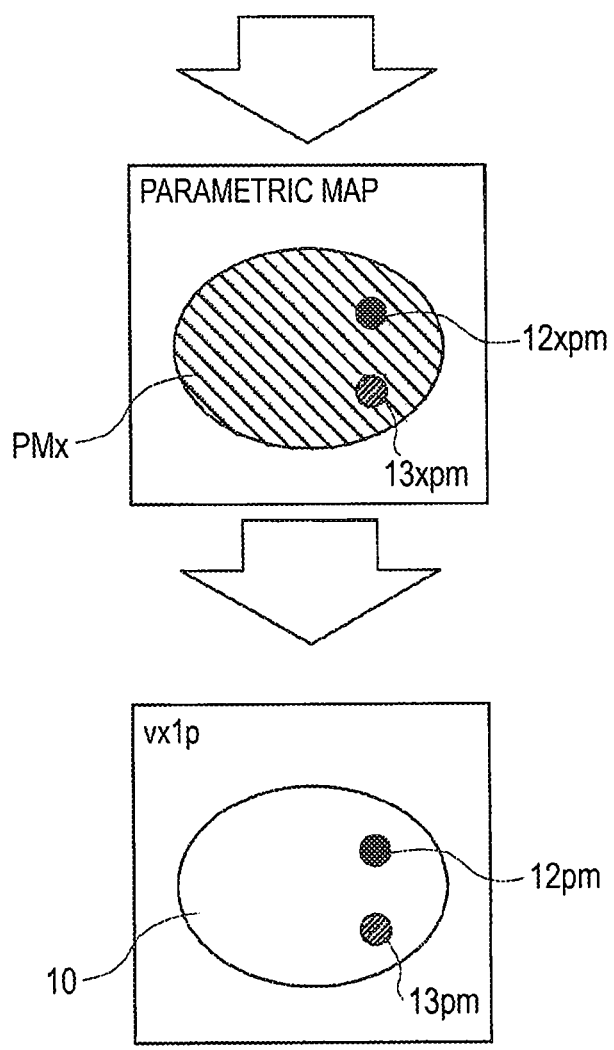
FIG. 13 is a diagram illustrating the generation of a parametric map based on time-series data in terms of registration in a comparative example (continuation of FIG. 12).

FIGS. 12 and 13 are diagrams illustrating the generation of the parametric map PMx based on time-series data to which registration according to the comparative example is added.

A hardware configuration of a medical image processing apparatus 100$x$ in the comparative example may be the same as the hardware configuration of the medical image processing apparatus 100 of the present embodiment. In the hardware configuration in the comparative example, a description will be given by attaching "x" to the end of a reference numeral.

In FIGS. 12 and 13, in the medical image processing apparatus 100$x$, a port 110$x$ acquires pieces of volume data vx1, vx2, and vx3 as time-series data. In the pieces of volume data vx1 to vx3, predetermined cross-sections and faults of the subject 10 as a subject are visualized (displayed). The region of the subject 10 includes the internal organ 11 moving independently of a lesion and affected parts 12 and 13 suspected to have a lesion.

Comparing the pieces of volume data vx1 to vx3 of respective phases with each other, similarly to FIG. 10, the luminance of voxels does not change much in the internal organ 11, the affected part 13, and the vicinities thereof, and the luminance of voxels changes greatly in the affected part 12 and the vicinity thereof.

A registration processing unit 164$x$ generates movement information based on the pieces of volume data vx1 to vx3. In addition, the registration processing unit 164$x$ deforms the pieces of volume data vx2 and vx3 in a direction opposite to the movement of the pieces of volume data vx2 and vx3 with respect to the volume data vx1 based on the movement information to obtain pieces of volume data vx2' and vx3'. That is, the pieces of volume data vx2 and vx3 are deformed to offset the movement of the affected parts 12 and 13 of the subject. As a result, the actual movement of the affected parts 12 and 13 is suppressed on the pieces of volume data vx2 and vx3, and the subject is supposed not to have moved.

A parametric map generation unit 163$x$ generates the parametric map PMx based on the deformed pieces of volume data vx1, vx2', and vx3'. The parametric map PMx includes a parameter 12$xpm$ corresponding to the affected part 12 and a parameter 13$xpm$ corresponding to the affected part 13. In FIG. 13, the parameters 12$xpm$ and 13$xpm$ are displayed at the positions of the affected parts 12 and 13 in the registration pieces of volume data vx1 to vx3. In FIG. 13, the parameters 12$xpm$ and 13$xpm$ are different values, indicate, for example, transitions of concentrations of different contrast mediums and have different display modes.

The display control unit 166$x$ generates superimposed volume data vx1$p$ by superimposing (synthesizing) the parametric map PMx on the volume data vx1. In the superimposed volume data vx1$p$, the internal organ 11, the parameter 12$xpm$ corresponding to the affected part 12, and the parameter 13$xpm$ corresponding to the affected part 13 are visualized. In the comparative example, unlike the present embodiment, the positions of the affected parts 12 and 13 in the pieces of volume data of respective phases are standardized, and thus the actual movement of the actually affected parts 12 and 13 cannot be read from the display and becomes unclear.

In this manner, according to the medical image processing apparatus 100 of the present embodiment, a parametric map PM is deformed in accordance with the movement of a tissue between a plurality of phases based on movement information without deforming time-series volume data. Therefore, the medical image processing apparatus 100 registers the parametric map PM without suppressing the movement of the tissue between the plurality of phases, and thus it is possible to easily confirm the movement of the tissue from volume data or the like. Further, unlike in the comparative example, in the medical image processing apparatus 100, time-series volume data is not seen so that a transition of concentration occurs at the same position, for example, by injection of a contrast medium while the volume data remains stationary after the termination of registration processing and a position where a transition of concentration is displayed in accordance with movement within volume data is also changed. Therefore, the medical image processing apparatus 100 can dynamically observe the movement within the volume data and also observe a transition of concentration.

In addition, the medical image processing apparatus 100 can confirm volume data before deformation even when the volume data is deformed due to the body movement of a subject as a subject. That is, unlike in the comparative example, the medical image processing apparatus 100 does not suppress the deformation of the volume data in accordance with reference volume data and thus can visualize the volume data before deformation. Accordingly, the medical image processing apparatus 100 can facilitate observation of the state of a deformable tissue in the subject.

In addition, the medical image processing apparatus 100 can use a dynamic region of interest r. For example, the medical image processing apparatus 100 may generate a parametric map PM using the dynamic region of interest r when a partial parametric map PM in volume data or a three-dimensional image is desired to be obtained, and may display a portion of the parametric map PM to be superimposed on a portion of the volume data or the three-dimensional image. When the region of interest r is set in any phase, the dynamic region of interest r moves following a tissue moving in another phase, based on the movement information. Therefore, a user can grasp the movement of the tissue of the subject corresponding to the region of interest r by observing the movement of the dynamic region of interest r. Further, when the movement of the tissue of the subject and the movement of the dynamic region of interest r are different, the user can detect that the movement information has an error by confirming the movement of the tissue of the subject 10 and the movement of the region of interest r which are displayed on the display 130.

In addition, the registration processing unit 164 may correct movement information by moving the region of interest r in any phase through the UI 120 and regenerating movement information based on the position of the moved region of interest r. In addition, the parametric map generation unit 163 may re-calculate a parametric map PM based on the corrected movement information. In this case, for example, the registration processing unit 164 may regenerate movement information by adding the movement of the region of interest r designated through the UI 120 as boundary conditions for calculating movement information and re-calculating the movement information.

As a result, the medical image processing apparatus 100 can correct movement information which does not match actual conditions and obtain meaningful movement information. Accordingly, it is possible to improve the accuracy of movement of the region of interest r and the accuracy of deformation of the parametric map PM based on the movement information.

As above, although various embodiments have been described with reference to the accompanying drawings, it is needless to say that the present disclosure is not limited to such examples. It will be apparent for those skilled in the art that various modification examples or corrected examples are conceivable within the scope recited in the claims, and it will be understood that these fall within the technical scope of the invention.

In the first embodiment, the parametric map generation unit 163 may use values (for example, an average value, a maximum value, a minimum value, a median value, and other values) which are obtained by collecting peripheral voxels (for example, a voxel v1 and eight surrounding voxels) positioned in the vicinity of the voxel v1, instead of voxels (voxel v1 (x, y, z)) in volume data. The parametric map generation unit 163 may generate a parametric map PM in the voxel v1 based on the values obtained by collecting the voxel values.

In the first embodiment, the parametric map generation unit 163 may generate a parametric map PM based on data derived based on volume data. For example, the parametric map generation unit 163 may reduce the resolution of the volume data and generate a parametric map PM based on the volume data with the reduced resolution. In this case, the resolution of the parametric map PM may also be reduced in accordance with the resolution of the volume data. The change of the resolution of the volume data may be performed manually through the UI 120 or may be performed automatically by the processing unit 160.

Further, for example, when both the resolution of the volume data v1 and the resolution of the volume data v2 illustrated in FIG. 10 are variable, the resolution of the volume data v1 and the resolution of the volume data v2 may be different from each other. In this case, the resolution of the parametric map PM1 corresponding to the volume data v1 and the resolution of the parametric map PM2 corresponding to the volume data v2 may be different from each other.

For example, the parametric map generation unit 163 may remove noise from volume data and generate a parametric map PM based on the volume data from which noise is removed. The noise removal may be performed, for example, through filtering for blocking signal components having a frequency of equal to or greater than a threshold value th3 (high-frequency components) and transmitting signal components having a frequency of less than the threshold value th3 (other than high-frequency components).

In the first embodiment, the display control unit 166 may display the parametric map PM generated based on the volume data v1 and v2 to be superimposed on the volume data v3. That is, the display control unit 166 may display the generated parametric map to be superimposed on volume data of a phase not related to the generation of the parametric map PM.

In addition, the processing unit 160 may interpolate and generate volume data at a time between imaging times of the pieces of volume data v1, v2, and v3 acquired as time-series data. The parametric map generation unit 163 may generate a parametric map PM corresponding to the interpolated volume data, deform the parametric map based on movement information, and visualize the parametric map.

One parametric map PM is generated in common for each phase. Pieces of volume data of all phases may not be used for the calculation of a parameter. Thus, for example, when the accuracy of imaging of volume data is low, the medical image processing apparatus 100 can exclude volume data having a low accuracy of imaging from volume data which is the base of calculation of the parameter. Accordingly, the medical image processing apparatus 100 can suppress deterioration of the accuracy of generation of a parametric map PM.

In the first embodiment, volume data as an acquired CT image is transmitted from the CT apparatus 200 to the medical image processing apparatus 100. Alternatively, volume data may be transmitted to a server or the like on a network and stored in the server or the like to be temporarily accumulated. In this case, when necessary, the port 110 of the medical image processing apparatus 100 may acquire volume data from the server via wired or wireless connection or may acquire volume data through any storage medium (not shown).

In the first embodiment, volume data as an acquired CT image is transmitted from the CT apparatus 200 to the medical image processing apparatus 100 through the port 110. It is assumed to include a case where the CT apparatus 200 and the medical image processing apparatus 100 are substantially combined as one product. In addition, this also includes a case where the medical image processing apparatus 100 is treated as a console of the CT apparatus 200.

In the first embodiment, an image is acquired by the CT apparatus 200 to generate volume data including information regarding the inside of the organism. However, an image may be acquired by any of other devices to generate volume data. Other devices include an MRI apparatus, a positron emission tomography (PET) device, a blood vessel angiographic device (angiography device), or other modality devices. In addition, the PET device may be used in combination with other modality devices.

In the first embodiment, a human body is described as a subject, but an animal body may also be used.

In the present disclosure, a program for realizing functions of the medical image processing apparatus of the first embodiment is supplied to the medical image processing apparatus through a network or various storage mediums, and the present disclosure is also applicable to a program read out and executed by a computer within the medical image processing apparatus.

As described above, in the medical image processing apparatus 100 of the above-described embodiment, an acquisition unit (for example, the port 110) images the same subject at least twice in time series to acquire a first medical image (for example, the volume data v1) and a second medical image (for example, the volume data v2). Based on the luminance at a first point (for example, an affected part 121) on the first medical image and the luminance at a second point (for example, an affected part 12m) indicating the same tissue as the tissue at the first point and having spatial coordinates different from the first point on the second medical image, the processing unit 160 calculates a first parameter (for example, the parameter 12pm) indicating a transition of the luminance at the first point. Based on the luminance at a third point (for example, an affected part 131) on the first medical image and the luminance at a fourth point (for example, an affected part 13m) indicating the same tissue as the tissue at the third point and having spatial coordinates different from the third point on the second medical image, the processing unit 160 may calculate a second parameter (for example, the parameter 13pm) indicating a transition of the luminance at the third point. In the first medical image, the processing unit 160 may superimpose the first parameter on the first point and superimpose the second parameter on the third point to visualize the first medical image. In the second medical image, the processing unit 160 may superimpose the first parameter on the second point and superimpose the second parameter on the fourth point to visualize the second medical image.

Therefore, the medical image processing apparatus 100 can associate the same tissues (for example, the affected parts 12l and 12m) before and after the movement in time series in a plurality of time-series medical images to calculate a parameter (for example, the parameter 12pm) indicating a transition of luminance accompanying the movement of the tissues. Movement information may be used for the association of the same tissues before and after the movement. The medical image processing apparatus 100 can visualize a parameter by superimposing the parameter on a medical image, and thus it is possible to simultaneously confirm a transition of luminance in any part of a subject in the medical image and the movement of the part of the subject, that is, to observe the movement of a fluid of any part.

In addition, the medical image processing apparatus 100 can derive parameters in accordance with the deformation of time-series medical images without suppressing the deformation of the medical images. In this case, the medical image processing apparatus 100 may registrate parameters of a parametric map PM in accordance with the movement of a tissue between a plurality of phases based on the movement information. Therefore, the medical image processing apparatus 100 can easily confirm the movement of the tissue without suppressing the movement of the tissue between the plurality of phases. In addition, a position where a transition of concentration is visualized varies depending on movement in the medical image, and thus the medical image processing apparatus 100 can dynamically observe the movement in the medical image and also observe a transition of concentration.

In addition, the medical image processing apparatus 100 can confirm a medical image before deformation even when the medical image is deformed due to the movement of the subject. Accordingly, the medical image processing apparatus 100 can facilitate observation of the state of a deformable tissue in the subject.

In this manner, the medical image processing apparatus 100 can support the observation of both the movement of the subject and the movement of a fluid inside the subject.

In addition, the acquisition unit may acquire a third medical image (for example, the volume data v3) which is obtained by imaging the subject in time series. The processing unit 160 may visualize the third medical image by superimposing the first parameter on a fifth point (for example, an affected part 12n) indicating the same tissue as a tissue at the first point and having spatial coordinates different from the first point on the third medical image.

The first parameter is generated based on the luminance at the first point and the luminance at the second point without considering the luminance at the fifth point. Also in this case, the medical image processing apparatus 100 can superimpose a parameter on a medical image not related to the calculation of the parameter. The parameter indicates a transition of luminance at any position in time-series medical images and may be common to the medical images. Therefore, the medical image processing apparatus 100 can suppress calculation of a parameter each time using a medical image on which the parameter is superimposed, can reduce a processing load of the medical image processing apparatus 100 related to the calculation of the parameter, and to improve the efficiency of use of the parameter.

In addition, the processing unit 160 may calculate the first parameter based on the luminance at the fifth point.

Accordingly, the number of points on a medical image used for the generation of a parameter is increased, and the number of phases related to the generation of parameters in time series is also increased. For this reason, the medical image processing apparatus 100 can improve the accuracy of reproduction of a transition of luminance indicated by the first parameter.

In addition, the medical image processing apparatus 100 may include an operation unit (for example, the UI 120) which receives the input (for example, setting) of a first region of interest (for example, the region of interest r11) in the first medical image. When the processing unit 160 receives the input of the first region of interest by the operation unit, a second region of interest (for example, the region of interest r21) including the same tissue as a tissue present in the first region of interest and having spatial coordinates differing from the first region of interest in the second medical image may be installed.

Accordingly, the medical image processing apparatus 100 can automatically install a region of interest in other medical images by manually installing a region of interest through the UI 120 in any one of the time-series medical images. In this case, the medical image processing apparatus 100 may use movement information. A region of interest is set automatically to visualize the region of interest, for example, in each of the medical images and a user can easily grasp the movement of a region of interest desired to be observed.

In addition, the operation unit may receive a change in coordinates of the second region of interest. When the coordinates of the second region of interest are changed, the processing unit 160 may calculate a third parameter on the assumption that the coordinates of the first region of interest and the changed coordinates of the second region of interest indicate the same tissue. The processing unit 160 may visualize the second medical image by superimposing the third parameter on the second region of interest of which the coordinates are changed, in the second medical image.

Accordingly, when the position of the second region of interest is changed manually through the UI 120, the medical image processing apparatus 100 can derive a parameter at a user's desired position in a medical image by re-calculating a parameter based on the second region of interest after the position of the second region of interest is changed. For example, as a case where the automatically set second region of interest is set manually, a case where the accuracy of movement information for associating corresponding points in time-series medical images with each other is low is considered.

Also in this case, the medical image processing apparatus 100 can newly associate corresponding points with each other by manually setting the original position of the second region of interest and can improve the accuracy of a derivation of a transition of luminance expressed by a parameter by calculating the parameter again.

At least one of the first medical image and the second medical image may be a medical image acquired in a state where a contrast medium is injected into the subject.

Accordingly, a change in luminance occurs in medical images arranged in time series due to flow-in or flow-out of a contrast medium with respect to a part of the subject. Accordingly, the medical image processing apparatus 100 calculates parameters indicating a transition of luminance due to the contrast medium and the concentration of the contrast medium, and thus it is possible to visualize the movement of the contrast medium while visualizing the movement of the subject in the medical images and to express both unshaped movement and the movement of the contrast medium in a state similar to the actual state.

The present disclosure is useful for a medical image processing apparatus, a medical image processing method, a medical image processing program, and the like, capable of observing both the movement of a subject and the movement of a fluid inside the subject.

What is claimed is:

1. A medical image processing apparatus comprising:
an acquisition unit; and
a processing unit, wherein
the acquisition unit acquires images of a same subject at least twice in time series to acquire a first medical image and a second medical image, and
the processing unit is configured to:
calculate a first parameter indicating a transition of luminance at a first point based on the luminance at the first point on the first medical image and luminance at a second point on the second medical image,
wherein the first and second points indicate a same tissue, and
spatial coordinates of the second point are different from spatial coordinates of the first point,
calculate a second parameter indicating a transition of luminance at a third point based on the luminance at the third point on the first medical image and luminance at a fourth point on the second medical image,
wherein the third and fourth points indicate a same tissue, and
spatial coordinates of the third point are different from spatial coordinates of the fourth point,
visualize the first medical image by superimposing the first parameter on the first point and by superimposing the second parameter on the third point in the first medical image; and
visualize the second medical image by superimposing the first parameter on the second point and by superimposing the second parameter on the fourth point in the second medical image.

2. The medical image processing apparatus according to claim 1, wherein
the acquisition unit acquires a third medical image of the subject in time series,
a fifth point indicates the same tissue on the third medical image,
spatial coordinates of the fifth point are different from the spatial coordinates of the first point, and
the processing unit visualizes the third medical image by superimposing the first parameter on the fifth point.

3. The medical image processing apparatus according to claim 2, wherein
the processing unit calculates the first parameter based on luminance at the fifth point.

4. The medical image processing apparatus according to claim 1, further comprising:
an operation unit that receives input of a first region of interest in the first medical image, wherein
when the operation unit receives the input of the first region of interest, the processing unit sets a second region of interest in the second medical image,
the first and second regions of interest indicate the same tissue, and
spatial coordinates of the second region of interest are different from spatial coordinates of the first region of interest.

5. The medical image processing apparatus according to claim 4, wherein
the operation unit receives a change in coordinates of the second region of interest, and
the processing unit is configured to
calculate a third parameter when the coordinates of the second region of interest are changed,
wherein coordinates of the first region of interest and the changed coordinates of the second region of interest indicate the same tissue, and
visualize the second medical image by superimposing the third parameter on the second region of interest of which the coordinates are changed, in the second medical image.

6. The medical image processing apparatus according to claim 1, wherein
at least one of the first medical image and the second medical image is a medical image acquired in a state where a contrast medium is injected into the subject.

7. A medical image processing method in a medical image processing apparatus, the medical image processing method comprising:
acquiring images of a same subject at least twice in time series to acquire a first medical image and a second medical image;
calculating a first parameter indicating a transition of luminance at a first point based on the luminance at the first point on the first medical image and luminance at a second point on the second medical image,
wherein the first and second points indicate a same tissue, and
spatial coordinates of the second point are different from spatial coordinates of the first point, calculating a second parameter indicating a transition of luminance at a third point based on the luminance at the third point on the first medical image and luminance at a fourth point on the second medical image, wherein the third and fourth points indicate a same tissue, and spatial coordinates of the third point are different from spatial coordinates of the fourth point, visualizing the first medical image by superimposing the first parameter on the first point and by superimposing the second parameter on the third point in the first medical image; and visualizing the second medical image by superimposing the first parameter on the second point and by superimposing the second parameter on the fourth point in the second medical image.

8. A medical image processing system causing a medical image processing apparatus comprising a processor to execute the medical image processing operations comprising:

acquiring images of a same subject at least twice in time series to acquire a first medical image and a second medical image;

calculating a first parameter indicating a transition of luminance at a first point based on the luminance at the first point on the first medical image and luminance at a second point on the second medical image, wherein the first and second points indicate a same tissue, and spatial coordinates of the second point are different from spatial coordinates of the first point, calculating a second parameter indicating a transition of luminance at a third point based on the luminance at the third point on the first medical image and luminance at a fourth point on the second medical image, wherein the third and fourth points indicate a same tissue, and spatial coordinates of the third point are different from spatial coordinates of the fourth point, visualizing the first medical image by superimposing the first parameter on the first point and by superimposing the second parameter on the third point in the first medical image; and visualizing the second medical image by superimposing the first parameter on the second point and by superimposing the second parameter on the fourth point in the second medical image.

\* \* \* \* \*

UNITED STATES PATENT AND TRADEMARK OFFICE
CERTIFICATE OF CORRECTION

PATENT NO. : 10,847,262 B2
APPLICATION NO. : 16/375932
DATED : November 24, 2020
INVENTOR(S) : Akihiko Izutani Page 1 of 1

It is certified that error appears in the above-identified patent and that said Letters Patent is hereby corrected as shown below:

In the Specification

Column 5, Line 10, "intensity projection (MW)" should read -- intensity projection (MIP) --

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*